Figure 1:
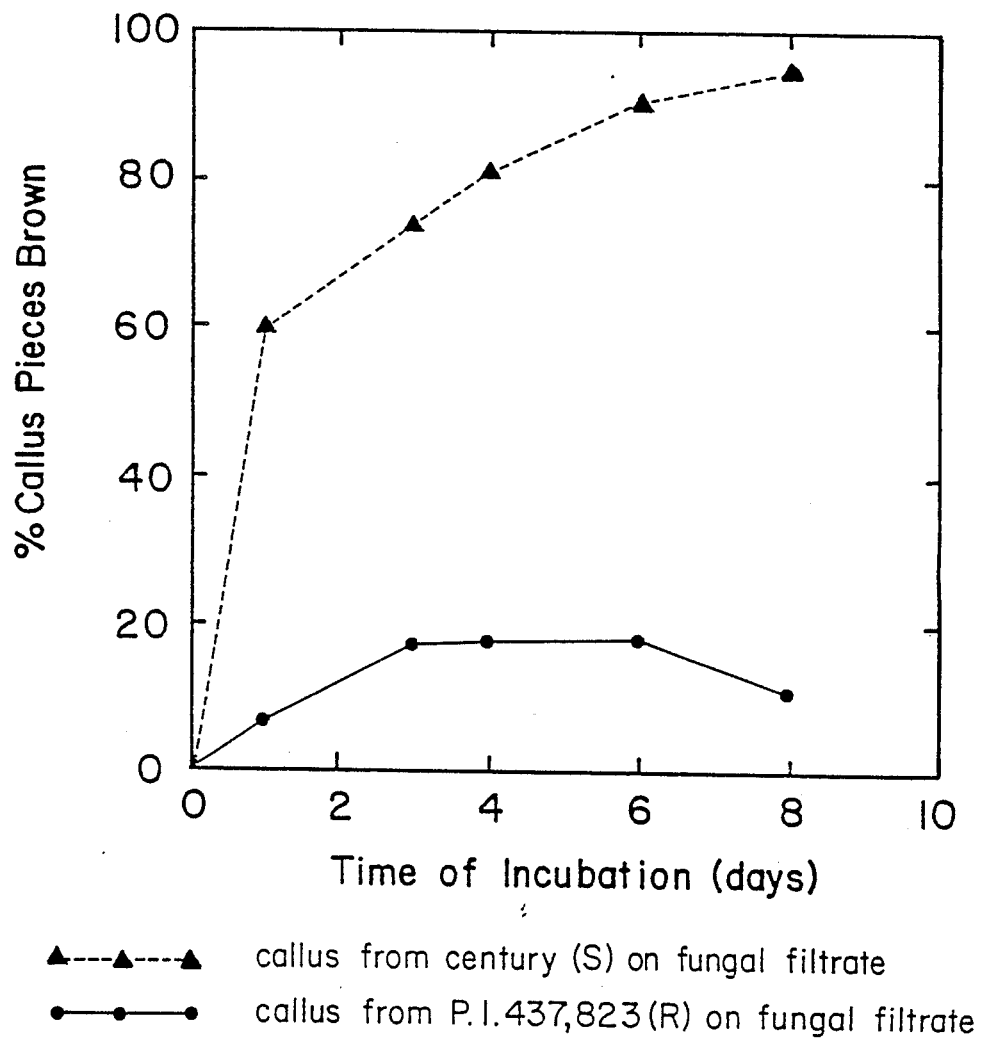

United States Patent [19]

Guan et al.

[11] Patent Number: 4,937,970
[45] Date of Patent: Jul. 3, 1990

[54] IN VITRO SCREENING FOR AND SELECTION OF GLYCINE MAX RESISTANT TO PHIALOPHORA GREGATA

[75] Inventors: Yong-Quan Guan, Urbana; Lynn E. Gray, Briarcliff; Jack M. Widholm, Champaign, all of Ill.

[73] Assignees: Lubrizol Genetics, Inc., Wickliffe, Ohio; The Board of Trustees of the University of Illinois, Urbana, Ill.

[21] Appl. No.: 778,384

[22] Filed: Sep. 20, 1985

[51] Int. Cl.$^5$ .................. A01B 79/00; C12Q 1/00
[52] U.S. Cl. .......................................... 47/58; 435/4; 435/171; 435/240.5; 424/93; 800/DIG. 26; 800/235; 47/DIG. 1
[58] Field of Search ............ 435/4, 171, 925, 240, 435/948; 424/93; 800/1; 47/58, DIG. 1

[56] References Cited

U.S. PATENT DOCUMENTS

| | | | |
|---|---|---|---|
| 4,443,971 | 4/1984 | Chaleff | 47/58 |
| 4,548,901 | 10/1985 | Christianson et al. | 435/241 |
| 4,616,100 | 10/1986 | McHughen | 47/58 |
| 4,642,411 | 2/1987 | Hibberd et al. | 800/1 |
| 4,684,612 | 8/1987 | Hemphill et al. | 435/240.5 |
| 4,761,373 | 8/1988 | Anderson et al. | 435/172.3 |

OTHER PUBLICATIONS

Christianson et al, *Science*, vol. 222, (1983), pp. 632-634.
Widholm et al, *Plant Cell Reports*, vol. 2, (1983), pp. 19-20.
Newell et al, *Plant Cell Tissue Organ Culture*, vol. 4, (1985), pp. 145-149.
Gray et al, *Plant Science*, vol. 47, (1986), pp. 45-55.
Chaleff, R., *Science*, vol. 219, (1983), pp. 676-682.
Sebastian et al, *Crop Science*, vol. 23, (1983), pp. 1214-1215.
Sebastian et al, *The Journal of Heredity*, vol. 76, (1985), pp. 194-198.
Gengenbach et al, *Proc. Natl. Acad. Sci. USA*, vol. 74, No. 11, (1977), pp. 5113-5117.
Sebastian et al, *Crop Science*, vol. 25, (1985), pp. 753-757.
Duncan et al, *Plant Breeding Reviews*, vol. 4, (1986), pp. 153, 162-173.
Gray, LE, (1971), Phytopathol. 61: 1410-1411, "Variation in Pathogenicity of Cephalosporium gregatum Isolates".
Gray et al, (1975), Phytopathol. 65: 89-90, "Evidence for Toxin Production by a Strain of Cephalosporium gregatum".
Haberlach et al, (1978), Plant Physiol. 62: 522-525, "Modification of Disease Resistance of Tobacco Callus Tissues by Cytokinins".
Helgeson, JP, (1983), in Use of Tissue Culture and Protoplasts in Plant Pathology, pp. 9-38, "Studies of Host-Pathogen Interactions in Vitro".
Hildebrand et al, (1986) in Biotechnology in Agriculture and Forestry, 2: Crops I, pp. 288-289, "Soybean [*Glycine max* (L.) Merr.], 2.1 and §2.2".

*Primary Examiner*—Robert J. Warden
*Assistant Examiner*—Carol A. Spiegel
*Attorney, Agent, or Firm*—Greenlee and Associates

[57] ABSTRACT

An in vitro method for screening *Glycine max* cells for resistance to a disease caused by *Phialophora gregata*, brown stem rot, is disclosed. The method is useful for identifying brown stem rot resistant soybean varieties. Means for selecting mutant soybean cells for resistance to a toxin produced by *P. gregata* is also provided, as are cells and plants selected by this process. The invention involves culture of soybean calli in the presence of a filtrate of used fungal growth medium.

19 Claims, 3 Drawing Sheets

▲---▲---▲ callus from century (S) on fungal filtrate
●——●——● callus from P.I.437,823 (R) on fungal filtrate
△---△---△ callus from century (S) on control filtrate
○——○——○ callus from P.I.437,823 (R) on control filtrate ▲----▲----▲ callus from century (S) on fungal filtrate
●——●——● callus from P.I. 437,823 (R) on fungal filtrate
△---△---△ callus from century (S) on control filtrate
○——○——○ callus from P.I. 437,823 (R) on control filtrate

IN VITRO SCREENING FOR AND SELECTION OF GLYCINE MAX RESISTANT TO PHIALOPHORA GREGATA

FIELD

The present invention is in the fields of plant genetic engineering and plant husbandry, and involves use of bio-affecting fermentates of unknown chemical structure, specifically fungal pathogen culture filtrates, in tissue culture for plant improvement.

BACKGROUND

Selection and screening in tissue culture for resistance of plant varieties to fungal pathogens is known to the art. Helgeson JP (1983) in *Use of Tissue Culture and Protoplasts in Plant Pathology*, eds. Helgeson JP and Deverall BJ, pp. 9-38, reviews this subject. Examples include resistance of potato (*Solanum tuberosum*) to *Phytophtora infestans* (Behnke M (1979) Theor. Appl. Genet. 55:69–71; Behnke M (1980) Theor. Appl. Genet 56:151–152) and to *Fusarium oxysporum* (Behnke M (1980) Z. Pflanzenzuchtg 85:254–258), resistance of maize (*Zea mays*) to *Helminthosporium maydis* race T (Gengenbach BG and Green CE (1975) Crop Sci. 15:645–649; Gengenbach BG et al. (1977) Proc. Natl. Acad. Sci. USA 74:5113–5117), resistance of rape seed (*Brassica napus*) to *Phoma lingam* (Sacristan MD (1982) Theor. Appl. Genet. 61:193–200 and 63:96), and resistance of soybeans *Glycine max*) to *Phytophthora megasperma* var. *sojae* (Holliday MJ and Klarman WL (1979) Phytopathol. 69:576–578). Haberlach GT et al. (1978) Plant Physiol. 62:522–525, showed that addition of cytokinins to the culture medium resulted in an improved differential response in culture of tobacco (*Nicotiana tabacum*) calli derived from resistant and susceptible plants to *Phytophthora parasitica* var. *nicotianae* race 0. However, they did not note a correlation between the improved differential response and the greening of the calli.

The art recognizes that resistance in culture (in vitro) and in vivo may not be correlated in all pathogen/plant systems. A genotype having in an intact plant a phenotype of resistance might be sensitive in culture. Conversely, a resistant callus might regenerate into a susceptible plant (see Helgeson, supra; Scowcroft WR et al., in Helgeson and Deverall, supra; Keen NT and Horsch R (1972) Phytopathol. 62:439–442). For instance, physiological responses specific to a particular tissue, organ, or state of differentiation may be different in plants than in cultured cells. Similarly, anatomical barriers present in plants are absent in cultured tissues. It is also recognized in the art that levels of gene expression in vivo and in vitro can be very different. For instance, Widholm J (1980) in *Plant Cell Cultures: Results and Perspectives*, eds: Sala F et al., provides an example of a gene specifying resistance to a toxic chemical which is expressed differently in cultured cells than in plants. If a correlation can be made between action of the pathogenic agent in vitro and in vivo the behavior of a pathogen/plant system becomes predictable from in vitro bioassays. The present invention teaches such a correlation.

Brown stem rot is a disease of soybeans caused by the fungus *Phialophora gregata*, which has often been identified in publications as *Cephalosporium gregatum* (Allington WB and Chamberlain DW (1948) Phytopathol. 38:793–802). Brown stem rot is a major pest of soybeans (e.g. see Seim D (Mid-Feb., 1985) pp. 24-D to 24-E) and is capable of reducing yields as much as 38% (Gray LE (1972) Plant Dis. Reptr. 56:580–581; Gray LE and Sinclair JB (1973) Plant Dis. Reptr. 57:853–854). In screening of soybean plants for brown stem rot resistance by conventional means, two resistance genes have been identified. There is a resistance/susceptibility gene, having resistance as the dominant allele. A modifier or minor nonallelic gene having resistance to brown stem rot as the dominant allele has also been detected (Sebastian SA and Nickell CD (1985) J. Hered. 76:194–198). Screening for resistance involves wounding and inoculation of the stems of individual plants (e.g. see Gray, supra; Gray and Sinclair, supra) or root inoculation with the fungus (Sebastian SA et al. (1983) Crop Sci. 23:1214–1215).

Isolates of *P. gregata* can be grouped into two classes, both of which cause vascular browning and one of which, Type I, produces a toxin which causes wilting and defoliation in sensitive soybeans, but not in resistant soybeans (Gray LE (1971) Phytopathol. 61:1410–1411; Gray LE and Chamberlain DW (1975) Phytopathol. 65:89–90). Three compounds, gregatin A, gregatin C, and gregatin D were characterized as causing some symptoms characteristic of brown stem rot on adzuki beans and of additionally inhibiting bacterial and fungal growth at concentrations lower than caused symptoms on plants; gregatin A was reported to give the most characteristic symptoms (Kobayashi K and Ui T (1975) Tetrahed. Lett. 47:4119–4122 and (1977) Physiol. Plant Pathol. 11:55–60). However, gregatin A is also produced by *Aspergillus panamensis*, which is not a plant pathogen (Anke H et al. (1980) J. Antibiot. 33:931–939). The structure of gregatin A as published by Kobayashi and Ui, supra, and Anke et al., supra, was found to be incorrect and was reassigned by Clemo NG and Pattenden G (1982) Tetrahed. Lett. 23:589–592. Reeder RT (1985) M.S. Thesis, University of Illinois at Urbana, showed that although gregatin A has some inhibitory effect on photosynthetic electron transport, it is not responsible for species-specificity and genotype-specificity in the brown stem rot disease.

SUMMARY

The present invention involves several steps. The fungus *Phialophora gregata* is cultured and the resulting used fungal growth medium is then filtered. The resulting fungus-free filtrate is then added to a medium capable of supporting soybean cell culture. After candidate resistant soybean cells are placed on this medium, resistant calli are identified. When many calli of a particular soybean genotype grow well on the soybean medium/-fungal filtrate combination, it indicates that the particular genotype is brown stem rot resistant; growth of few or no calli indicates sensitivity of the genotype to the species-specific, plant genotype-specific toxin produced by *P. gregata*. Any resultant growing calli descended from a susceptible plant genotype are mutants resistant to the toxin. Should soybean plants be regenerated from such mutant calli, the resultant plants will be resistant to brown stem rot.

Before the disclosure of the present invention, there was no way to identify in tissue culture soybean varieties resistant to brown stem rot. Neither was there any way to select in culture mutant soybean cell lines expressing resistance to brown stem rot. Therefore, one object of the present invention is to provide a means for identifying cultured soybean tissues displaying resistance to brown stem rot, the in vitro resistance being predictive of resistance displayed by soybean plants of the same genotype. Towards this goal, other objects are to provide a means for screening extant soybean varieties for resistance to brown stem rot and to provide means to select in vitro mutants resistant to brown stem rot wherein the resistant cells are descended from sensitive cells. A further object is to provide a bioassay capable of detecting the species-specific and genotype-specific toxin produced by *P. gregata* responsible for the symptoms of brown stem rot. Further objects will be apparent from the following disclosure.

The present invention provides a number of advantages when compared to prior art methods for screening for brown stem rot resistance by inoculating plants with fungus under greenhouse or field conditions. The invention does not involve dissemination of *P. gregata* in the environment, thereby eliminating risk of introduction of the fungus into uninfested fields. The present invention is quantitative, being capable of comparing degrees of resistance. Experimental variation is reduced. For example, interference by other pathogens or pests is eliminated by the in vitro assay which improves scoring of resistance/susceptibility. Also, inocula used in prior art methods lack uniformity. Furthermore, in practice testing for resistance often depends on the endogenous fungus in a field; often the level and biotype of *P. gregata* is not known until after soybeans have been planted. The present invention is more reliable, not being subject to environmental risks (e.g. bad weather) associated with field tests, and is readily practiced in all seasons of the year. The present invention can, in many cases, provide an earlier evaluation of soybean genotypes. It also provides means for screening and/or selection of resistant soybean genotypes produced in tissue culture without first requiring candidate tissues to be regenerated into plants. Use of the present invention to select in culture soybean cells resistant to brown stem rot toxin may be used as an early step in the production of soybean plants regenerated from those cells. The regenerated plants may be found to have increased levels of brown stem rot resistance or to have resistance genes at novel genetic loci. Availability of novel resistance will be useful in efforts to breed brown stem rot resistant soybeans; *P. gregata* mutants which overcome a plant genotype's (i.e. a plant variety's) resistance are much less likely to develop on soybeans having resistant alleles at different loci than genotypes resistant at single loci.

Although many examples exist of in vitro screening of and selection for plant cells resistant to the effects of a fungal toxin, in vivo and in vitro resistances are not always predictive of each other (see Background). It is well known in the art of plant tissue culture that a gene expressed in a plant may not be expressed in cultured tissue derived from that plant; conversely, a gene expressed in tissue culture may be "turned off" in regenerated plants. This is especially true in cases where resistance or susceptibility of whole plants does not correlate with resistance or sensitivity to toxins of cultured cells derived from those plants. Furthermore, not only must behavior in vivo and in vitro correlate for differing plant genotypes, but pathogenic and nonpathognic characteristics of fungi or fungal by-products in vivo and in vitro must also be correlated. In vitro methods cannot be used to screen or select plant genotypes resistant to a pathogen in the absence of such correlations. However, once such correlations have been established, it is possible to predict the response of a plant to a pathogen from the in vitro behavior tissue having the same genotype. We established such a correlation for a soybean disease caused by *P. gregata*, brown stem rot. We have discovered that a brown stem rot resistance gene which is expressed in a plant is also expressed in culture. Disclosure of this discovery will allow the art to screen soybean varieties in vitro for resistance to brown stem rot using either a herein disclosed bioassay or other bioassays which may be developed based on the present discovery. Additionally, this discovery forms the basis for production of brown stem rot resistant plants derived from brown stem rot susceptible plants by identification of mutant cells expressing brown stem rot resistance in culture. Also disclosed herein are several factors whose control we have found to be important for efficient bioassay of brown stem rot resistance; these factors are not always crucial in other in vitro plant disease bioassays.

BRIEF DESCRIPTION OF THE FIGURES

FIG. 1 presents a time course of observed percentage of browning calli. The circles represent data for calli derived from a brown stem rot resistant (R) genotype, P.I. 437,823, while the triangles represent data for calli derived from a brown stem rot sensitive (S) cultivar, Century.

FIG. 2 presents a time course of changes in tissue fresh weight. Symbols are as in FIG. 1, filled circles representing data from P.I. 437,823 calli (R) grown in the presence of S1 fungal filtrate and filled triangles representing data from Century calli (S) grown in the presence of S1 fungal filtrate. Additionally, the open circles and open triangles represent data of calli derived from P.I. 437,823 (R) and Century (S), respectively, grown in the presence of control filtrate.

FIG. 3 presents a time course of changes in triphenyltetrazolium chloride (TTC) assays of tissue viability. Symbols are as in FIG. 2.

DETAILED DESCRIPTION OF THE INVENTION

Identification of soybean cells having brown stem rot resistant genotype and expressing a brown stem rot resistant phenotype combines the specific teachings of the present disclosure with a variety of techniques and expedients known in the art. In most instances, alternative expedients exist for each stage of the overall process. Expedients which may be changed include, but are not limited to, fungus isolate, species-specific, genotype-specific toxin preparation protocol, the soybean genotype (e.g. the specific cultivar, variety, or plant introduction) from which the cultured cells are derived, soybean cell culture protocols, the bioassay medium, amounts of toxin added to the bioassay medium, the type and form of the soybean tissue placed on the bioassay medium, the conditions of assay, the means for evaluation and/or scoring of bioassay results, means for soybean plant regeneration, and the like, all of which present alternative process steps which those of ordinary skill in the art are able to select and use to achieve the desired result without undue experimentation. For instance, as novel means are discovered for regeneration of soybean cell cultures into soybean plants, these regeneration methods may be incorporated into the invention disclosed herein. The fundamental aspect of the invention is the unexpected discovery that soybean plant resistance to brown stem rot in vivo is correlated with soybean cell resistance in vitro to a species-specific, genotype-specific toxin produced by *Phialophora gregata*; i.e. in soybeans a gene for brown stem rot resistance can be expressed and its expression recognized both in vivo and in vitro. It is crucial that any modifications of the herein disclosed bioassay be tested with different races of *P. gregata*, both pathogenic and nonpathogenic, and with different varieties of soybean, both sensitive and resistant, as well as with a control assay that omits toxin. Such tests can be made without undue experimentation by those of ordinary skill in the art.

We have discovered that *P. gregata* secretes into its medium a toxin distinct from the previously identified gregatin toxins. This toxin can be prepared in crude form by filtering solid material out of used culture medium in which a pathogenic isolate of *P. gregata* had been grown. Pathogenic isolates are defined herein as the Type I isolates described by Gray LE (1971) Phytopathol. 61:1410–1411. Type I isolates cause defoliation and leaf symptoms as reported by Allington WB and Chamberlain DW (1948) Phytopathol. 38:793–802, in addition to vascular discoloration. For example, S1 is pathogenic on Century (see Examples). Type II isolates, which cause vascular discoloration but not foliar symptoms, are herein considered nonpathogenic. This toxin is best characterized by its effect on soybean tissues of brown stem rot susceptible soybean varieties. When cuttings comprising stem and leaf tissues are placed in this crude, cell-free filtrate, the cuttings exhibit diagnostic symptoms of brown stem rot: vascular browning and chlorosis and necrosis of leaves. By way of comparison, published studies have shown gregatin A not to cause such a full range of brown stem rot symptoms. We have also shown (Example 7) that this crude filtrate can be used in vitro to identify resistant and susceptible soybean cultures. Tissues derived from susceptible plants are susceptible in vitro and tissues derived from resistant plants are resistant in vitro.

The toxin produced by *P. gregata* which is the active component in the bioassay of the present invention is a species-specific and genotype-specific toxin. These specificities are recognizable by functional tests. The species-specific property was indicated by the lack of effect of filtrates from the culture medium of an isolate of *P. gregata* which is not pathogenic to soybeans but which is pathogenic to adzuki beans; adzuki beans are not of the genus Glycine. Another functional test for presence of the toxin in a solution was the effect of similarly prepared toxin preparations derived from different strains of *P. gregata*. In general, a method for toxin preparation is suitable for use in this bioassay if it yields preparations from nonpathogenic isolates which do not inhibit callus growth and if it yields preparations from pathogenic isolates which kill calli. The genotype-specific property was indicated by the response of soybean calli to the presence of the toxin in filtrates of growth media of pathogenic isolates; calli derived from resistant soybeans grew in the presence of the toxin while calli derived from susceptible soybeans did not grow but died. Any method for preparation of the toxin or soybean cells which does not preserve the biological relationships between pathogenicity and nonpathogenicity in vivo and toxicity in vitro (i.e. in culture) is not a suitable modification of the bioassay disclosed herein.

Any method for preparation of the *P. gregata*-produced, species-specific, genotype-specific toxin may be used as long as the biological properties of the toxin are preserved. In the preferred embodiments, a pathogenic isolate of the fungus *P. gregata* is cultured in a glucose-soybean stem extract medium. The choice of *P. gregata* isolate is important. We have found the isolate S1, which is available to the public as NRRL 13198 (ARS Culture Collection, Northern Regional Research Center, USDA-ARS-NCR, 1815 N. University St., Peoria, Ill. 61604 USA), to work very well as a pathogenic isolate in the present invention. However, those skilled in the art may identify other isolates of *P. gregata* which may readily substitute for isolate S1. In the preferred embodiments, toxin is supplied to the bioassay medium as a crude filtrate of used S1 growth medium. However, a purified toxin preparation may be substituted for the crude preparation. Purification protocols may be developed using adaptations of the herein disclosed bioassay. For instance, a fraction which when derived from isolate SI is toxic to sensitive calli but not to resistant calli would contain the toxin. As an additional control, a similarly prepared fraction derived from a culture of a nonpathogenic culture should be compared with the pathogen-derived preparation and with a preparation derived from unused culture medium; both resistant and sensitive soybean cells should grow similarly to each other in the presence of this control preparation. In addition, they should grow similarly to resistant cells cultured in the presence of the S1-derived preparation.

We found it very useful to adjust the pH of the fungal filtrate and control filtrate to match the pH of the plant culture medium of the bioassay medium. Without such adjustment, the differentiation between resistant and sensitive cells in the presence of fungal filtrate was reduced. However, the bioassay could work without pH adjustment.

The amount of toxin added to the medium is also very important. One of ordinary skill in the art may find, without undue experimentation, that dilutions other than the 7-fold dilution most commonly exemplified herein are advantageous in modified protocols. For instance, varying the fungus strain or fungal growth conditions could lead to differences in toxin concentration in the fungal filtrate. Differences in callus growth habits may affect uptake of toxin, e.g. a more compact callus may require higher toxin levels for maximum growth differentials between resistant and sensitive calli. Optimum toxin concentration, e.g. filtrate dilution, should always be established, and is herein exemplified in Example 7.

Any method for culture and evaluation of Glycine cells may be used as long as genotypes sensitive in vivo remain phenotypically sensitive in vitro and genotypes resistant in vivo remain phenotypically resistant in vitro. For example, changes could be made to the herein disclosed protocols if changes in prebioassay culture conditions were made, as long as Century calli remained sensitive to the toxin and P.I. 437,823 calli remained resistant. Similarly, changes could be made in bioassay conditions and bioassay evaluation if similar results with Century and P.I. 437,823 are obtained.

In the preferred embodiments soybean seeds were surface sterilized and germinated on a solidified medium lacking hormones (MS−, Murashige T and Skoog F (1962) Physiol. Plant. 15:473–497). After four or five days, pieces of stems and leaves were placed on a medium known to be supportive of soybean callus growth (Phillips GC and Collins GB (1979) Crop Sci. 19:59-64). This medium, supplemented with an artificial 2,4-dichlorophenoxyacetic acid (2,4-D), is designated herein L2DNK. After one or two subcultures on the medium, with about two to about three weeks between transfers, callus pieces were then transferred to soybean callus growth medium (SCGM) medium.

We found the condition of the tissue to be important. The differentiation between the responses of sensitive and resistant callus was greatest if the callus was green during the bioassay. This greening was promoted by the inclusion of cytokinins in bioassay medium. It is known in the art that cytokinins such as benzyladenine (BA) promote greening in culture. The bioassay also worked on nongreen tissues. We are not aware of any publications correlating improved selection or screening for resistance to a pathogen's toxin with greening of callus tissue.

The size of the transferred calli was also found to be important. Uniformity of size increased the reliability and comparability of the results. Callus pieces ranging in size between 1 mg and 5 mg were tested; 2 mg pieces gave the best differentiation between resistant and sensitive calli. Optimum results were obtained when calli were cultured and assayed under diffuse light. Calli were then maintained on SCGM for at least a month, being transferred at two week intervals, before transfer to bioassay dishes.

In the preferred embodiments, bioassay dishes had a solidified medium consisting of a soybean callus growth medium (SCGM: MS$^-$ supplemented with 2,4-D to promote tissue growth and BA to promote tissue greening) diluted with quantity of fungal filtrate or control filtrate. Dilution of SCGM by addition of fungal or control filtrate did not appear to significantly or adversely affect callus growth, nor did addition of glucose in the control filtrate make interpretation of results difficult.

In the preferred embodiments the effects of toxin on sensitive tissues were assessed in three ways: browning of sensitive tissues, greater increase of fresh weight of resistant calli than sensitive calli, and decreased cellular viability of sensitive calli when compared to resistant calli in triphenyltetrazolium chloride (TTC) assays. Interpretation of these assays is discussed in Example 6. Browning of tissue could be scored in as little as one day, TTC assay could be scored in as little as two days, while fresh weight measurement were best made in six to eight days. It will be understood by those skilled in the art that other means to assess the effect of the *P. gregata*-produced, species-specific, genotype-specific toxin on growth of Glycine tissue in culture may be substituted for the three measures discussed above, if the novel measure yields results which correlate well with the results obtained from the measures exemplified herein.

The bioassay of the present invention may be combined with other methods known to the art of plant tissue culture or with methods which the art may yet discover. In particular, the bioassay serves as a means for identifying natural (i.e. spontaneous), mutagen-induced, or somaclonal genetic variants resistant to the brown stem rot toxin but derived from brown stem rot susceptible soybean plants. The step of identifying genetic variants can refer to either the screening of individual genotypes or the selecting of resistant genotypes present in a population which includes both resistant and susceptible cells. Glycine cells growing in culture will naturally comprise mixed population with genetic variants arising from natural mutations or somaclonal variants. These cells may be grown up into calli which can then be screened individually for resistance to toxin or may be cultured in the presence of toxin, thereby selecting resistant genetic variants. Those in the art will recognize that selecting and screening have in common that genotypes growing in the presence of toxin are noted and may be further propagated while genotypes not growing are either ignored, discarded, or not observed; herein the term identifying subsumes the terms screening and selecting. It may sometimes be advantageous to mutagenize soybean cells in vitro before single cell cloning with chemical or physical mutagens in order to increase the proportion of mutant cells in a population of cultured cells; such methods and considerations are well known and understood in the art. When callus pieces of soybean tissue are placed on a bioassay dish, only resistant cells within the calli will be observed to grow. These growing tissues can then be introduced into soybean regeneration protocols known to the art. The callus pieces either may be derived from single cell clones or may not be clonally derived; if not, growing tissue masses may be found and will most likely be of single cell origin, as is understood in the art. Alternatively, a suspension culture or protoplasts can be plated onto bioassay dishes. When doing so, it may prove advantageous to immobilize the plated cells by embedding them in alginate or a low melting-temperature agar, both methods well known to the art. The presence of feeder cells in the bioassay medium may also be advantageous; such cells are best derived from a non-Glycine legume species. The concentration of toxin may need to be changed from that used in bioassays of calli and the plating density of candidate Glycine cells will need to be determined; the proper toxin concentration and plating density can be determined by those of ordinary skill in the art without undue experimentation. An additional alternative is inclusion of toxin in the medium of a suspension culture. As described with screened calli, the resultant toxin resistant calli which are observed to grow can then be introduced into a soybean regeneration protocol known to the art.

After a brown stem rot resistant plant is identified by using the bioassay described herein as a screen or is produced by regenerating natural (i.e. spontaneous), mutagen-induced, or somaclonal genetic varients after using the bioassay as a screen or as a basis of selection, the resultant resistant plant may be entered into a soybean breeding program. Sexual crosses of transformed plants with agronomically important cultivars yield initial hybrids. These hybrids can then be self-fertilized or, more advantageously, back-crossed with plants of the desired genetic background. Progeny are continuously screened by the bioassay of the present invention or by prior art methods for brown stem rot resistance. In this manner, after a number of rounds of back-crossing and selection or of self-fertilization and selection soybean plants can be produced which are thoroughly inbred and genetically stable. If back-crossing is used, the plants will have a genotype essentially identical to the agronomically-desired parents but additionally will be resistant to brown stem rot.

EXAMPLES

1. Culture of brown stem rot fungus

*Phialophora gregata*, sometimes identified in the literature as *Cephalosporum gregatum*, was grown in a glucose-soybean stem extract medium (the dextrose-soybean stem extract medium of Allington WB and C Chamberlain DW (1948) Phytopathol. 38:793-802). Green soybean stems grown under field conditions were harvested and, after being stripped of leaves, were oven-dried. The dried stems were pulverized in a Wiley mill and stored at less than $-5°$ C. Five grams of dried soybean stem powder were boiled in 400 ml of deionized water for 20-25 min. After filtering through cheesecloth, 10-25 g (usually 16 g) of glucose was added to the green filtrate which was then made up to 1 L. 100 ml aliquots were placed in 250 ml Ehrlenmeyer flasks which were then autoclaved. The glucose-stem extract medium generally had a pH of 6.0-6.2; the pH was not adjusted.

*P. gregata* mycelia were on a soybean stem extract medium lacking glucose which was solidified with 1.6% BACTO TM Agar(Difco, Detroit, Mich.). inoculated by addition of one or two plugs of fungus cut out of a maintenance culture with a sterile needle, the plugs being about 8 mm square and comprising both fungus and agar. Cultures were grown in the dark aerobically at 23° C. for 4-5 weeks; liquid cultures were not shaken.

Alternative methods for growth of *P. gregata* fungus which are known to the art or which may be discovered may be incorporated into the protocols of the present invention as long as the species-specific, genotype-specific toxin is produced.

2. Preparation of fungal and control filtrates

After growth of brown stem rot fungus in glucose-soybean stem extract medium, fungal mycelia are removed from the culture by filtration through Whatman Number 1 filter paper. The resulting used culture medium, also referred to herein as fungal extract, had a pH in the range of pH 4.5 to pH 4.8 if S1 had been grown; other fungal strains might result in used medium having a less acid pH. The pH was adjusted to about pH 5.8 with either KOH or HCl as was appropriate; gross adjustments were done with 1 N solutions and fine adjustments with a 0.1 N solution. The pH-adjusted fungal filtrate was then filter sterilized by being forced through a 0.45 μm pore nitrocellulose filter (Millipore number 12309, Bedford, Mass.).

Control filtrate was prepared essentially as described above for fungal filtrate except that no fungus was cultured and no inoculum plug was added. The control filtrate was essentially unused, pH-adjusted, filter-sterilized, fungal growth medium.

3. Preparation of bioassay plates

Bioassay plates were prepared by addition of varying volumes of fungal or control filtrate to fixed volume (20 ml in a 100×15 mm Petri dish or 10 ml in a 60×15 mm dish) of soybean callus growth medium (SCGM, Table 1), an adaptation of the medium of Murashige T and Skoog F (1982) Physiol. Plant. 15:973–997. 2,4-dichlorophenoxyacetic acid (2,4-D) of SCGM stimulated callus growth while the benzyladenine (BA) promoted greening of tissue. Typically a variable volume of fungal filtrate or control filtrate was added to a fixed volume of SCGM. For example, a five-fold dilution of filtrate in a 100 mm diameter Petri dish had 5 ml of filtrate added to 20 ml of SCGM. The SCGM was cooled to 50° C. before addition of fungal filtrate. Tissue was always transferred to the fungal filtrate/SCGM combination the same day the Petri dishes were prepared.

4. Initiation and maintenance of soybean callus cultures

Soybean (*Glycine max*) seeds were surface sterilized by soaking in 20% Chlorox TM for 15 to 20 min. After being rinsed three times with sterile water, the seeds were then put on MS− medium (the medium of Murashige T and Skoog F (1962) Physiol. Plant. 15:473–497, without phytohormones) for germination. Leaf or stem tissue was removed four or five days after germination; calli derived from leaves or stems seemed to behave identically in bioassays. Tissue pieces were initially put on L2DNK medium (Table 1, derived from PC-L2 of Phillips GC and Collins GB (1979) Crop. Sci. 19:59–64) and were cultured covered with white paper (to provide diffuse light) at 28° C. with a 16 hr light, 8 hr dark cycle. The resulting friable, mostly white callus tissue was subcultured one or two times on L2D, 16–20 days between subcultures. Subcultures were generally initiated with 1.5–2.0 mm pieces of tissue and were subcultured when calli were about 7–10 mm in diameter. Calli were then transferred to and maintained on SCGM for at least one month before selection; calli was subcultured every two weeks.

5. Bioassay

Pieces of soybean callus weighing about 2 mg were placed on bioassay medium. Generally, about 16 calli would be put on a 60×15 mm Petri dish while about 40 pieces were put on a 100×15 mm dish. Calli were cultured under diffuse light at 28° C. as described above.

Calli were observed visually daily; green calli were relatively unaffected by any brown stem rot toxin while brown calli were relatively affected by the toxin and contained many dead cells. The percentage of browning calli resulting from any particular combination of fungal filtrate, dilution, and soybean cultivar was recorded.

At 0, 2, 4, 6, and 8 days after placement on bioassay medium, 5 calli were taken and placed in a tightly-sealable Petri dish so as not to decrease in weight due to drying. The previously tared Petri dishes were then weighed to obtain a fresh weight. Cell viability was then assayed by addition of 3 ml of a 8 mg/ml solution of triphenyltetrazolium chloride (TTC) buffered by 0.05 M sodium phosphate, pH 7, to the tissue (Towill LE and Mazar P (1975) Can. J. Bot. 53:1097–1102). After incubation at 23° C. for 5 hr, the red, reduced triphenyltetrazolium was extracted from 10 mg of tissue with 1.0 ml of 95% ethanol. The extracted red color was quantitated by measurement in a spectrophotometer (1 cm light path) of absorbance at 485 nm ($OD_{485}$).

6. Bioassay interpretation

These three indicators, percent browning, increases in fresh weight, and TTC assays, illuminate different aspects of callus response to the presence of a toxin. Percent browning was an all-or-nothing measure. Each individual callus is scored as either green or brown; there was nothing in between. Therefore, cells can be dead in a green callus and some cells can be alive in a callus scored brown. Increases in fresh weight could be misleading when the increases are small. Callus could grow slightly before starting to die in response to the presence of toxin, presumably primarily by cell enlargement. TTC assays measured cell viability, being capable of detecting a few live cells among many dead cells. However, what was actually being measured was mitochondrial electron transport activity; this was related to but not strictly proportional to numbers or proportions of cells which remained alive. Though they measured different parameters, combination of the three indicators gave a very reliable indication of toxicity of an extract. In addition, experience in performance of this bioassay has shown that these three indicators could be predictive of each other. For example, an experiment that resulted in the browning of many calli usually showed little increase in fresh weight and no increase in the amount of TTC reduced (i.e. no increase in $OD_{485}$) by mitochondria of living cells. Conversely, an experiment that resulted in few calli becoming brown usually showed a large increase in tissue fresh weight and produced a significant increase in reduction of TTC as indicated by an increased $OD_{485}$ reading. There was not a direct correlation between fresh weight measurement and TTC assays, as a callus could in some situations grow but still had low viability. Of the three indicators, percent browning was the easiest to quantitate while being, due to its all-or-nothing nature, least reliable. TTC assays were most accurate, being able to detect a few live cells in a dying mass.

7. Representative results

Calli derived from resistant and sensitive lines of soybean performed similarly when grown on a 16-fold dilution of a culture filtrate of brown stem rot race S1 (NRRL 13198). A 4-fold dilution of fungal extract led to death of half of the brown stem rot resistant-line-derived calli and almost all the sensitive lines, while a 3-fold dilution killed almost everything but a few resistant calli. A 7-fold dilution of fungal extract was found to be optimum in bioassays, giving the greatest difference in response of calli derived from a resistant (R) genotype (P.I. 437,823) and a sensitive (S) cultivar (Century). Those skilled in the art will recognize that the optimum dilution for this bioassay may vary somewhat from the 7-fold dilution disclosed herein and that the optimum dilution for other conditions may be discovered without undue experimentation.

Percent browning, fresh weight, and $OD_{485}$ as measured in TTC assays are graphed against time of culture on bioassay medium having race S1 filtrates diluted 7-fold into SCGM and are presented in the Figures.

Figure 2:
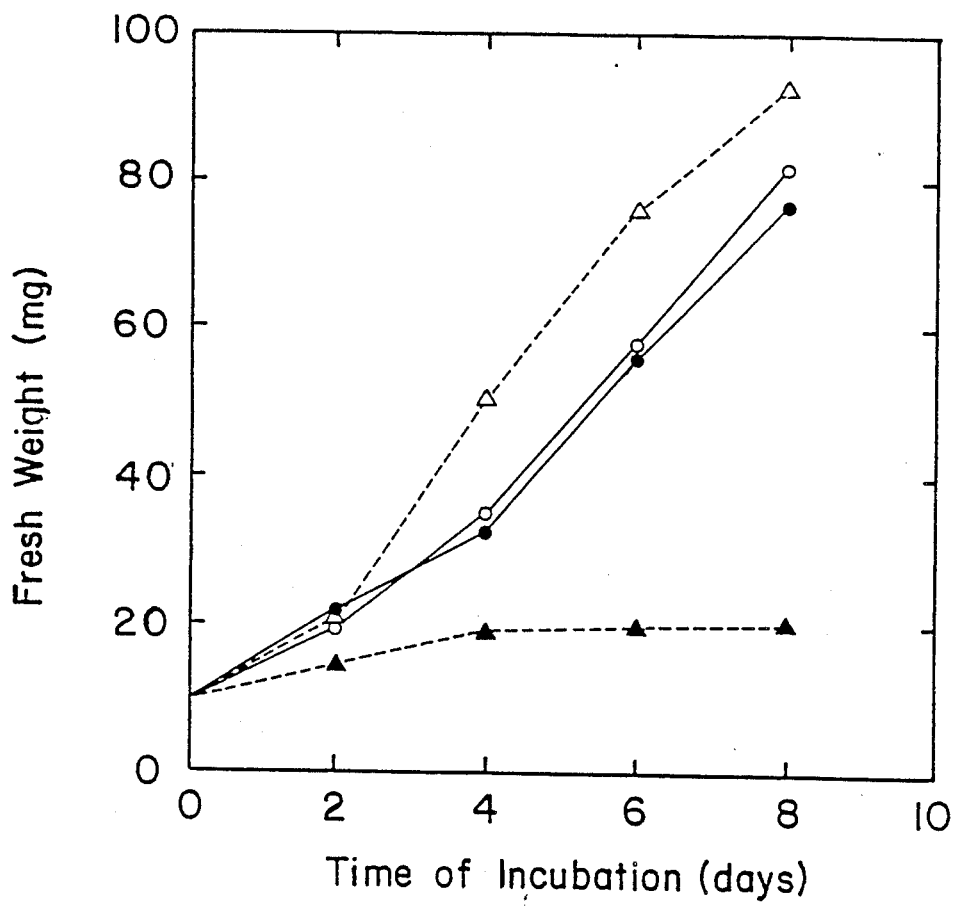
Figure 3:
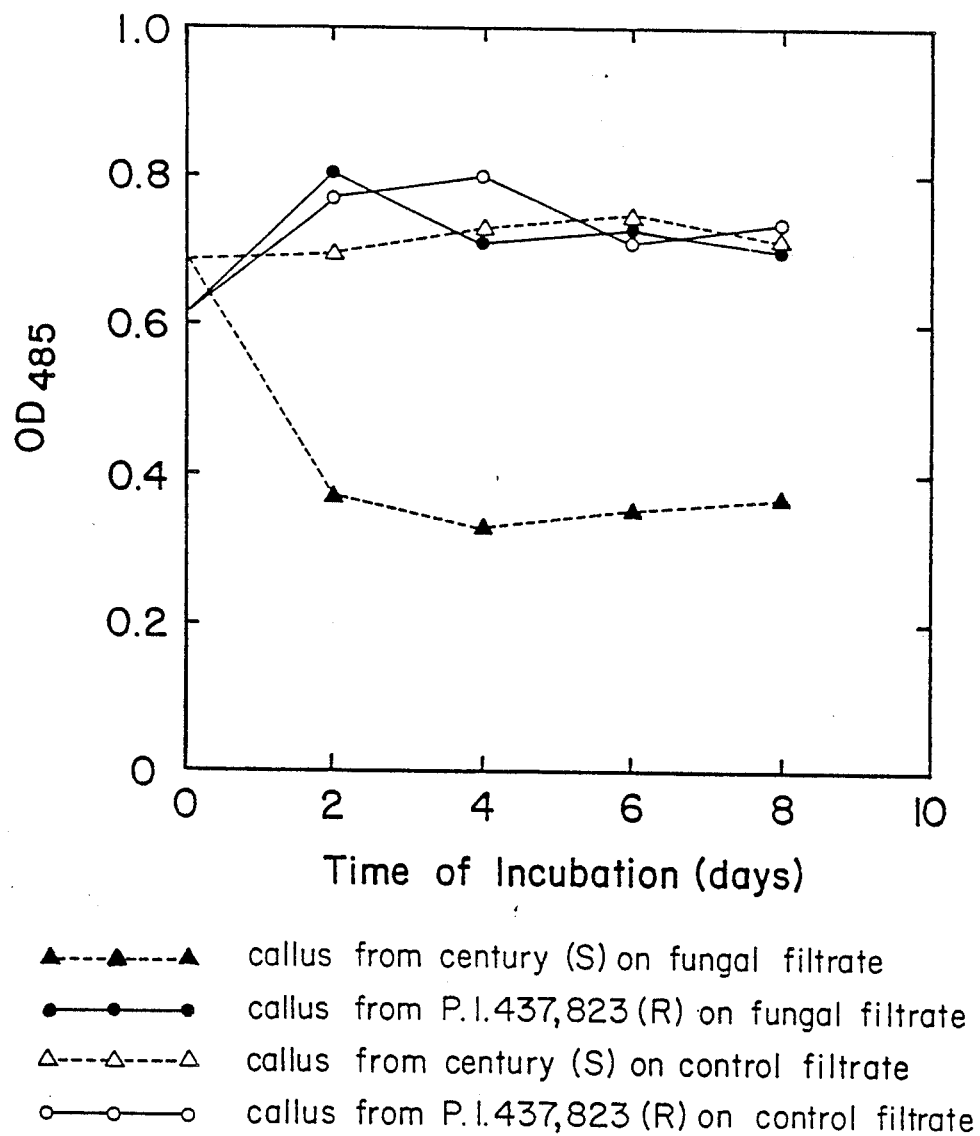

In the presence of fungal filtrate, three-fifths of the Century (S) calli was rated as brown after one day and only about one-twentieth was green at the end of an eight day experiment. In contrast, P.1. 437,823 (R) calli always rated less than one-fifth brown (FIG. 1). This indicated that cells derived from brown stem rot resistant soybeans were resistant to fungal by-products in culture while cells derived from sensitive soybeans tended to be killed in culture by fungal by-products. At the end of an eight day exposure to fungal filtrate, P.I. 437,823 (R) calli increased in fresh weight more than 7-fold while Century (S) showed a minimal increase. On control filtrate Century (S) and P.I. 437,823 (R) calli grew on control filtra about the same, about 9-fold and about 8-fold, respectively (FIG. 2). This indicated that a fungal by-product significantly inhibited growth of sensitive, but not resistant, soybean cells. The increased growth of the calli grown in the presence of control filtrate relative to the resistant callus grown on fungal filtrate supplemented SCGM was probably the result of improved callus culture conditions (e.g. higher concentration of glucose) due to use of unused fungal growth medium.

Between two and eight days, TTC assay of both resistant and sensitive calli in the presence of control filtrate gave $OD_{485}$ readings virtually identical to that of resistant calli (P.1. 437,823) grown in the presence of fungal filtrate, indicating that calli from resistant lines were fully viable in the presence of the fungal by-products. In contrast, callus from the sensitive cultivar Century gave significantly lower $OD_{485}$ readings, indicating loss of cellular viability in the presence of a fungal by-product.

Calli derived from Century, a soybean cultivar sensitive to brown stem rot, were placed on 6-fold dilutions of fungal filtrates. After eight days fresh weight increase and TTC reduction were measured. Three strains (S1, I8, and Asgro-5) of P. gregata which are pathogenic to soybeans, one strain (5–22) which is pathogenic to adzuki beans but not soybeans, and one nonpathogenic strain (IT) were used to make fungal filtrates. As described elsewhere, control tissue was cultured in the presence of control filtrate derived from glucose-stem extract medium which had not had fungus cultured in it. The results of replicate experiments are disclosed in Table 2. There were no significant differences in increase in fresh weight. However, TTC assays showed that cell viability was greatly reduced when sensitive calli were exposed to filtrates of cultures of pathogenic fungi (S1, I8, and Asgro-5) while exposure to filtrates of a nonpathogenic fungus (IT) did not reduce viability below that of the control. Soybean calli exposed to filtrate of a culture of 5–22, a Japanese isolate of P. gregata which is pathogenic to adzuki bean plants but not to soybean plants, remained as viable as control tissues. This demonstrated that the bioassay response was due to a species-specific toxic factor in the filtrates not produced by 5–22, and not to a toxic factor having toxicity to many taxa, such as gregatin A. Consistent with this interpretation is our finding that all isolates listed in Table 2 (S1, I8, I7 and 1101NP) produced gregatin A and that toxic activity in the bioassay was not proportional to measured gregatin A concentrations.

TABLE 1

|  | $MS^-$ | SCGM | L2DNK |
|---|---|---|---|
| $NH_4NO_3$ | 1650 | 1650 | 1000 |
| $KNO_3$ | 1900 | 1900 | 2100 |
| $CaCl_2.2H_2O$ | 440 | 440 | 600 |
| $MgSO_4.7H_2O$ | 370 | 370 | 435 |
| $KH_2PO_4$ | 170 | 170 | 325 |
| $NaH_2PO_4.H_2O$ | — | — | 85 |
| KI | 0.83 | 0.83 | 1.0 |
| $H_3BO_3$ | 6.2 | 6.2 | 5.0 |
| $MnSO_4.4H_2O$ | 22.3 | 22.3 | — |
| $MnSO_4.H_2O$ | — | — | 15.0 |
| $ZnSO_4.7H_2O$ | 8.6 | 8.6 | 5.0 |
| $Na_2MoO_4.2H_2O$ | 0.25 | 0.25 | 0.4 |
| $CuSO_4.5H_2O$ | 0.025 | 0.025 | 0.1 |
| $CoCl_2.6H_2O$ | 0.025 | 0.025 | 0.1 |
| $Na_2.EDTA$ | 37.23 | 37.23 | — |
| $FeSO_4.7H_2O$ | 27.95 | 27.95 | 25.0 |
| Inositol | 100 | 100 | 250 |
| Nicotinic acid | 0.5 | 0.5 | — |
| Pyroxidine.HCl | 0.5 | 0.5 | 0.5 |
| Thiamine.HCl | 0.1 | 0.1 | 2.0 |
| Glycine | 2.0 | 2.0 | — |
| 2,4-Dichlorophenoxyacetic acid (2,4-D) | — | 0.1 | 0.4 |
| 4-Amino-3,5,6-trichloropicolinic | — | — | 0.06 |

TABLE 1-continued

|  | MS⁻ | SCGM | L2DNK |
|---|---|---|---|
| acid (picloram) | | | |
| benzyl adenine | — | — | 0.10 |
| α-Naphthaleneacetic acid (NAA) | — | — | 4.6 |
| Kinetin | — | 2.15 | 2.15 |
| Sucrose | 30 g/l | 30 g/l | 25 g/l |
| Agar | 8 g/l | 8 g/l | 8 g/l |
| pH | pH 5.7 | pH 5.7 | pH 5.8 |

All quantities are mg/l unless otherwise noted.

TABLE 2

| Fungal strain | Fungus characteristic | Fresh weight at day 8 (mg) | TTC at day 8 ($OD_{485}$) |
|---|---|---|---|
| S1 | pathogenic | 21.8 ± 3.9 | 0.252 ± 0.046 |
| I8 | pathogenic | 23.6 ± 9.6 | 0.265 ± 0.110 |
| IT | nonpathogenic | 107.6 ± 23.9 | 0.751 ± 0.034 |
| 1101NP | nonpathogenic | 125.1 ± 1.8 | 0.693 ± 0.036 |
| — | control filtrate | 125.0 | 0.731 |

At time 0, fresh weights were about 10 mg and TTC assays had $OD_{485}$ of 0.744 ± 0.050.

We claim:

1. A method for identifying the presence of brown stem rot resistance in a Glycine plant comprising growing cells of said plant in in vitro cell culture in the presence of a *Phialophora gregata* Type I-produced, species-specific, genotype-specific toxin, observing the viability of said cells, and identifying the presence of brown stem rot resistance in plants whose cultures show viability in the presence of said toxin.

2. The method according to claim 1 wherein said toxin is produced by *P. gregata* NRRL 13198.

3. The method according to claim 1 wherein said Glycine cells are cells of *Glycine max*.

4. The method according to claim 1 wherein said toxin is comprised in a culture filtrate which is produced by growing *P. gregata* Type I in culture, followed by filtering the used *P. gregata* Type I growth medium to produce said filtrate.

5. The method according to claim 4 wherein said *P. gregata* growth medium is a glucose-soybean stem extract medium.

6. The method according to claim 4 wherein said culture filtrate comprising said toxin is subjected to filter sterilization.

7. The method according to claim 1 wherein said step of growing Glycine cells in the presence of said toxin is preceded by a step of preculturing Glycine cells.

8. The method according to claim 7 wherein said cultured cells are cells of *Glycine max*.

9. The method according to claim 8 wherein said cultured *Glycine max* cells are callus cells.

10. The method according to claim 9 wherein said step of growing *Glycine max* cells in the presence of said toxin comprises placing an approximately 2 mg piece of *Glycine max* callus onto a solidified medium comprising said toxin.

11. The method according to claim 10 wherein said callus cells are green.

12. The method according to claim 11 wherein said step of culturing callus cells is done in the presence of a cytokinin.

13. The method according to claim 8 wherein said cultured *Glycine max* cells are produced in a suspension culture.

14. The method according to claim 13 wherein said cultured *Glycine max* cells are further cultured on a solidified medium prior to being grown in the presence of said toxin.

15. The method according to claim 13 wherein said cultured *Glycine max* cells produced in suspension culture are plated onto a solidified medium comprising said toxin.

16. A method for selection of a brown stem rot resistant variant soybean cell from an in vitro cell culture derived from a brown stem rot susceptible soybean plant comprising the steps of (a) culturing Glycine cells derived from the brown stem rot susceptible soybean plant such that the cell population comprises genetic variants, followed by (b) culturing the Glycine cells in the presence of a *Phialophora gregata* toxin, followed by (c) identifying and selecting a variant Glycine cell which is viable in the presence of said toxin as resistant to brown stem rot.

17. The method according to claim 16 wherein said Glycine cells are *Glycine max* cells.

18. A method for producing a brown stem rot resistant Glycine plant which comprises the steps of (a) selecting a brown stem rot resistant variant soybean cell from an in vitro cell culture derived from a brown stem rot susceptible soybean plant by culturing Glycine cells derived from said susceptible soybean plant such that the cell population comprises variants, followed by culturing said Glycine cells in the presence of a *Phialophora gregata* toxin and identifying and selecting a variant Glycine cell which is viable in the presence of said toxin as resistant to brown stem rot, followed by (b) regenerating said brown stem rot resistant Glycine plant from said variant Glycine cell resistant to brown stem rot.

19. The method of claim 18 wherein said brown stem rot resistant Glycine plant is a *Glycine max* plant and said variant cell is derived from a brown stem rot susceptible *Glycine max* plant.

* * * * *

UNITED STATES PATENT AND TRADEMARK OFFICE
CERTIFICATE OF CORRECTION

PATENT NO. : 4,937,970

DATED : July 3, 1990

INVENTOR(S) : Yong-Quan Guan, et al

It is certified that error appears in the above-identified patent and that said Letters Patent is hereby corrected as shown below:

On the title page item [73], the assignees, should read:
"Lubrizol Genetics, Inc., Wickliffe, Ohio, The Board of Trustees of the University of Illinois, Urbana, Illinois; and United States of America, The, as represented by the Secretary of Agriculture.
At column 3, line 64, "nonpathognic" should read --nonpathogenic--.
At column 4, line 3, "behavior tissue" should read --behavior of tissue--.
At column 7, line 48, "measurement were" should read --measurements were--.
At column 9, line 17, "100" should not be in bold-face type.
At column 9, bridging lines 23 and 24, "Mich.) inocu-lated" should read --Mich.). Liquid cultures were inoculated--.
At column 9, line 65, "Typically a" should read --Typically, a--.
At column 11, line 63, "filtra" should read --filtrate--.

Signed and Sealed this

Twenty-first Day of April, 1992

Attest:

HARRY F. MANBECK, JR.

*Attesting Officer*   *Commissioner of Patents and Trademarks*